(12) United States Patent
Bernard et al.

(10) Patent No.: US 9,395,299 B2
(45) Date of Patent: Jul. 19, 2016

(54) METHOD FOR DETERMINING THE BIDIRECTIONAL REFLECTANCE DISTRIBUTION FUNCTION (BRDF) OF A SURFACE

(75) Inventors: Stefano Bernard, Orbassano (IT); Giuseppe Varalda, Orbassano (IT)

(73) Assignee: C.R.F. SOCIETA CONSORTILE PER AZIONI, Orbassano (Turin)

( * ) Notice: Subject to any disclaimer, the term of this patent is extended or adjusted under 35 U.S.C. 154(b) by 859 days.

(21) Appl. No.: 13/305,327

(22) Filed: Nov. 28, 2011

(65) Prior Publication Data
US 2012/0253749 A1   Oct. 4, 2012

(30) Foreign Application Priority Data

Mar. 30, 2011  (EP) .................................... 11160527

(51) Int. Cl.
| | |
|---|---|
| *H04B 1/38* | (2015.01) |
| *G01C 3/10* | (2006.01) |
| *G06F 3/01* | (2006.01) |
| *G06F 3/02* | (2006.01) |
| *G01N 21/55* | (2014.01) |
| *G06T 15/50* | (2011.01) |

(52) U.S. Cl.
CPC .............. *G01N 21/55* (2013.01); *G06T 15/50* (2013.01)

(58) Field of Classification Search
CPC ..................................................... G06T 15/50
USPC ................. 702/104, 140, 154, 181, 188, 189; 356/237.2
See application file for complete search history.

(56) References Cited

U.S. PATENT DOCUMENTS

| | | | | |
|---|---|---|---|---|
| 7,286,218 | B2 * | 10/2007 | Tiemeyer et al. | .......... 356/237.2 |
| 7,436,505 | B2 * | 10/2008 | Belyaev et al. | ............ 356/237.2 |
| 7,689,035 | B2 * | 3/2010 | Mallick et al. | ................ 382/163 |

OTHER PUBLICATIONS

Yanxiang Lan et al., "Condenser-Based Instant Reflectometry", Computer Graphics Forum, vol. 29, No. 7, Sep. 1, 2010, pp. 2091-2098.
Pei-Feng Hsu et al., "Bi-Directional Reflectivity of Surfaces with Anisotropic Roughness on the Wafer Backside", Advanced Thermal Processing of Semiconductors, 2007, 15th International Conference on IEEE PI, Oct. 1, 2007, pp. 231-238.

(Continued)

*Primary Examiner* — Gregory J Toatley
*Assistant Examiner* — Felix Suarez
(74) *Attorney, Agent, or Firm* — Heslin Rothenberg Farley & Mesiti P.C.; Victor A. Cardona, Esq.

(57) ABSTRACT

A method for determining the bidirectional reflectance distribution function of a generally plane rough surface of a specimen made of a given material includes acquiring a refractive index of the material, the spectrum of total reflectance measured on the specimen, and the geometry of the profile of the surface. The geometry is determined by: detecting the height and approximating the surface of the specimen as a distribution of plane triangular microfaces. For each direction of incidence of the light on the surface of the specimen and for each direction of observation there is determined the angular orientation of the microfaces contributing to reflecting in a specular way the light incident in the direction of observation. The Fresnel factor defining the specular reflectance of each microface is determined. The total BRDF is determined as the sum of a Lambertian component and of a specular component.

3 Claims, 4 Drawing Sheets

(56) References Cited

OTHER PUBLICATIONS

Qunzhi Z. Zhu et al., "Correlation of Angle-Resolved Light Scattering with the Microfacet Orientation of Rough Silicon Surfaces", Optical Engineering, vol. 44, No. 7, Jan. 1, 2005, pp. 073601-073612.

Ashikhmin M et al., "A Microfacet-Based BRDF Generator", Computer Graphics, Siggraph 2000 Conference Proceedings. New Orleangs, LA, Jul. 23-28, 2000, pp. 65-74.

European Search Report for corresponding European Application No. 11160527.5, dated Sep. 2, 2011.

* cited by examiner

METHOD FOR DETERMINING THE BIDIRECTIONAL REFLECTANCE DISTRIBUTION FUNCTION (BRDF) OF A SURFACE

CROSS REFERENCE TO RELATED APPLICATIONS

This application claims priority to European Patent Application No. 11160527.5, filed Mar. 30, 2011, the entire disclosure of which is incorporated herein by reference.

FIELD OF THE INVENTION

The present invention relates to a method for determining the bidirectional reflectance distribution function (BRDF) of a generally plane rough surface of a specimen made of a given material, typically a plastic material.

The invention regards a method that can be applied, in particular, to specimens of opaque plastic material, whether neutral or coloured, bulk-pigmented, the surface profile of which is completely random and isotropic or else characterized by regular structuring.

There are not currently available, to the knowledge of the applicant, methods of the type referred to above that enable a convenient and precise determination of the BRDF of surfaces of the type indicated above. There is felt on the other hand the need, in a wide range of fields, to provide a tool of this sort. For example, in the automotive industry, a method of this type could be advantageously used as aid in the design of dashboards made of plastic material, for evaluating the characteristics of reflectance of the dashboard and checking that they are compatible with the requirements of good visibility for the driver.

OBJECT AND SUMMARY OF THE INVENTION

Consequently, a main object of the invention is to provide a simple and precise method for determining the BRDF of a surface.

According to the invention, said object is achieved thanks to the characteristics indicated in the annexed Claim 1, the contents of which form an integral part of the present description.

BRIEF DESCRIPTION OF THE FIGURES

The invention will now be described with reference to the annexed drawings, in which.

DESCRIPTION OF THE PREFERRED EMBODIMENT OF THE INVENTION

Figure 1:
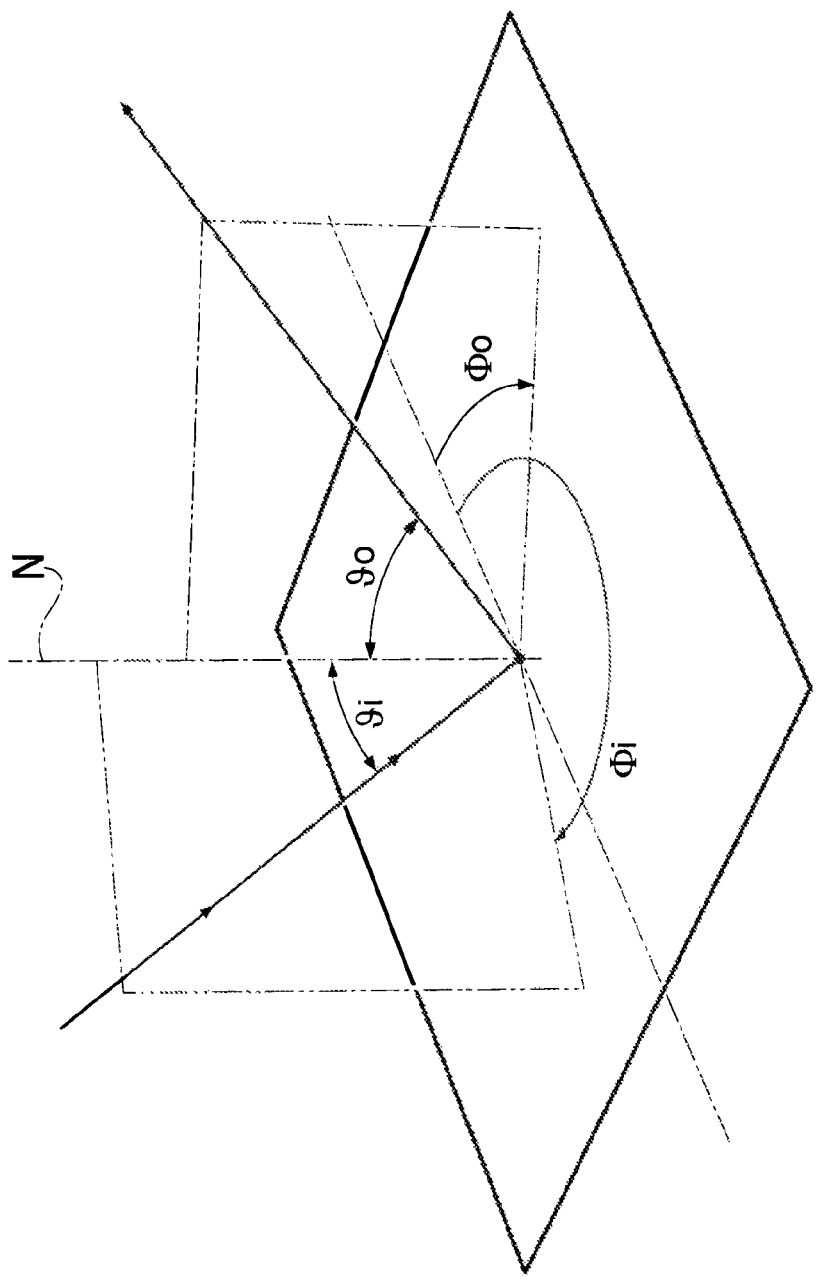
FIG. 1 is a schematic representation of the angles that identify the direction of a ray of light impinging in a point P on the surface S and the direction of observation.

The method according to the invention is used for determining the bidirectional reflectance distribution function (BRDF) of a generally plane rough surface of a specimen made of a given material.

The method envisages in the first place acquiring the following input data:
refractive index of the material;
spectrum of total reflectance measured on the specimen; and
geometry of the profile of said surface.

Refractive Index

In the preferred embodiment the following two options are envisaged for the user:
a. entering directly the value of the refractive index of the material of which the specimen is made, obtained by direct measurements with purposely provided measuring tools (for example, ellipsometer) or from the relevant literature;
b. indicating the plastic material chosen from a series of materials proposed.

In case a., the datum is immediately supplied to the algorithm, whereas in case b., the value of the refractive index is linked to the choice made by the user from among the materials proposed and available in a database. For example, the following plastic materials may be proposed (an average indicative value in the visible spectrum of the corresponding refractive index is given in brackets):
ABS (1.55)
PC/ABS (1.59)
PP (1.49)

Spectrum of Total Reflectance (Specularity Included)

In the preferred embodiment, the following three options are envisaged for the user:
entering manually the spectrum of total reflectance, specularity included, through the successive indication of orderly pairs (wavelength, total reflectance); this first case can arise, for example, with data obtained from the literature or from purposely provided measuring tools (for example, spectrophotometer with integrating sphere) in the case where the latter do not supply at output a text file;
loading a spectrum of total reflectance from text files containing at least two columns, the first of which indicates the measurement wavelengths, and the second the respective total reflectance, specularity included; this second case can arise, for example, when the spectrum of total reflectance is obtained by direct measurement with measuring tools (for example, spectrophotometer with integrating sphere) that supply at output text files;
entering the colorimetric co-ordinates (for example in the CIELAB reference system, L*a*b*); this third case can arise when there is not available a reference plastic specimen from which to obtain, by direct measurement, the spectrum of total reflectance, but only colorimetric co-ordinates in a given reference system (for example in the format L*a*b*) are available.

The first two cases are similar because they immediately lead to having a series of orderly pairs (wavelength, total reflectance) representing the spectrum of total reflectance, specularity included, of the plastic specimen.

The third case requires the need to resort to an algorithm for estimation of the spectrum of total reflectance starting from the colorimetric co-ordinates available.

The particular case of the algorithm of estimation of the reflectance spectrum starting from the CIELAB colorimetric co-ordinates is described hereinafter. It is based on random generation of spectra of total reflectance starting from the sum of a finite number of base spectra (for example, four and indicatively referred to as red, green, blue, and cyan). For each random spectrum thus generated the CIELAB colorimetric co-ordinates and the consequent difference ΔE with respect to the target colorimetric co-ordinates are calculated. The algorithm continues in the random generation of reflectance spectra until:

the value of $\Delta E$ reached is lower than a pre-determined threshold (for example, lower than 1.0);

the user blocks generation, it being possible, however, to check the shape of the reflectance spectrum corresponding to the lowest $\Delta E$ reached up to that moment and possibly restore the generation of random spectra.

In essence, and limitedly to the specific example with a base made up of 4 base spectra, the algorithm is based upon repeated and random generation of a set of four $w_i$ numbers comprised between 0 and 1. Each set of four $w_i$, together with a fixed and pre-determined set of four base spectra $S_i$, defines a spectrum of total reflectance obtained as the sum of the base spectra $S_i$, each weighted with the corresponding weight $w_i$:

$$S_{rnd} = \sum_i w_i \cdot S_i$$

Should the maximum value reached by $S_{rnd}$ exceed 100%, the spectrum $S_{rnd}$ is rescaled to the maximum value of 100%.

Of each of the spectra $S_{rnd}$ thus obtained the colorimetric co-ordinates $L_{rnd}^* a_{rnd}^* b_{rnd}^*$ are calculated, considering a reference illuminant (for example, D65) and using the classic formulas of colorimetry, here not given for reasons of brevity.

Each set of three $L_{rnd}^* a_{rnd}^* b_{rnd}^*$ is compared with the target set of three $L^* a^* b^*$ through the calculation of the difference $\Delta E$, calculated as:

$$\Delta E = \sqrt{(\Delta L^*)^2 + (\Delta a^*)^2 + (\Delta b^*)^2}$$

The interface displays to the user the lowest value of $\Delta E$ reached up to that moment, obviously storing the corresponding random set of four $w_i$.

The cycle of random generation of sets of four $w_i$ continues until:

1. the value of $\Delta E$ drops below a pre-determined threshold (for example, 1.0), in which case the cycle is blocked autonomously, and the set of four $w_i$ that, together with the fixed set of four spectra $S_i$, describes the best estimate of the desired reflectance spectrum is returned;
2. the user blocks manually and temporarily the generation cycle, displaying the spectrum $S_{rnd}$ associated to the lowest value of $\Delta E$ achieved up to that moment; the user then decides whether to force the algorithm to return said spectrum $S_{rdn}$ as best estimate, or else whether to resume the cycle and continue random generation of the sets of four $w_i$.

Geometry of the Profile of the Surface of the Specimen

Figure 3:
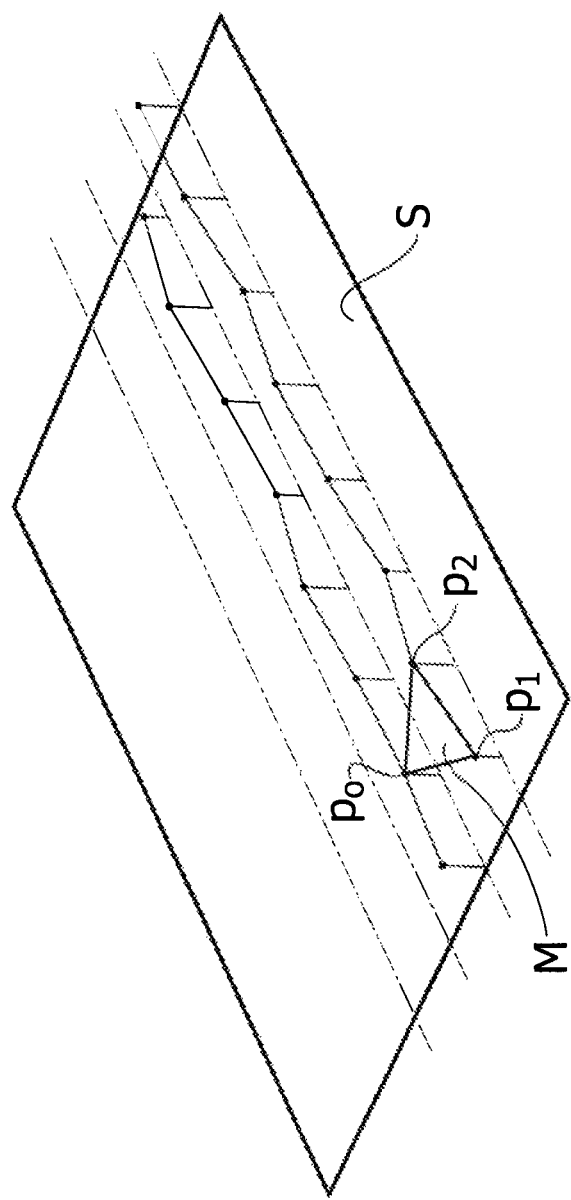
FIG. 3 illustrates the method of reconstruction of the surface as the sum of triangular microfaces.
Figure 4:
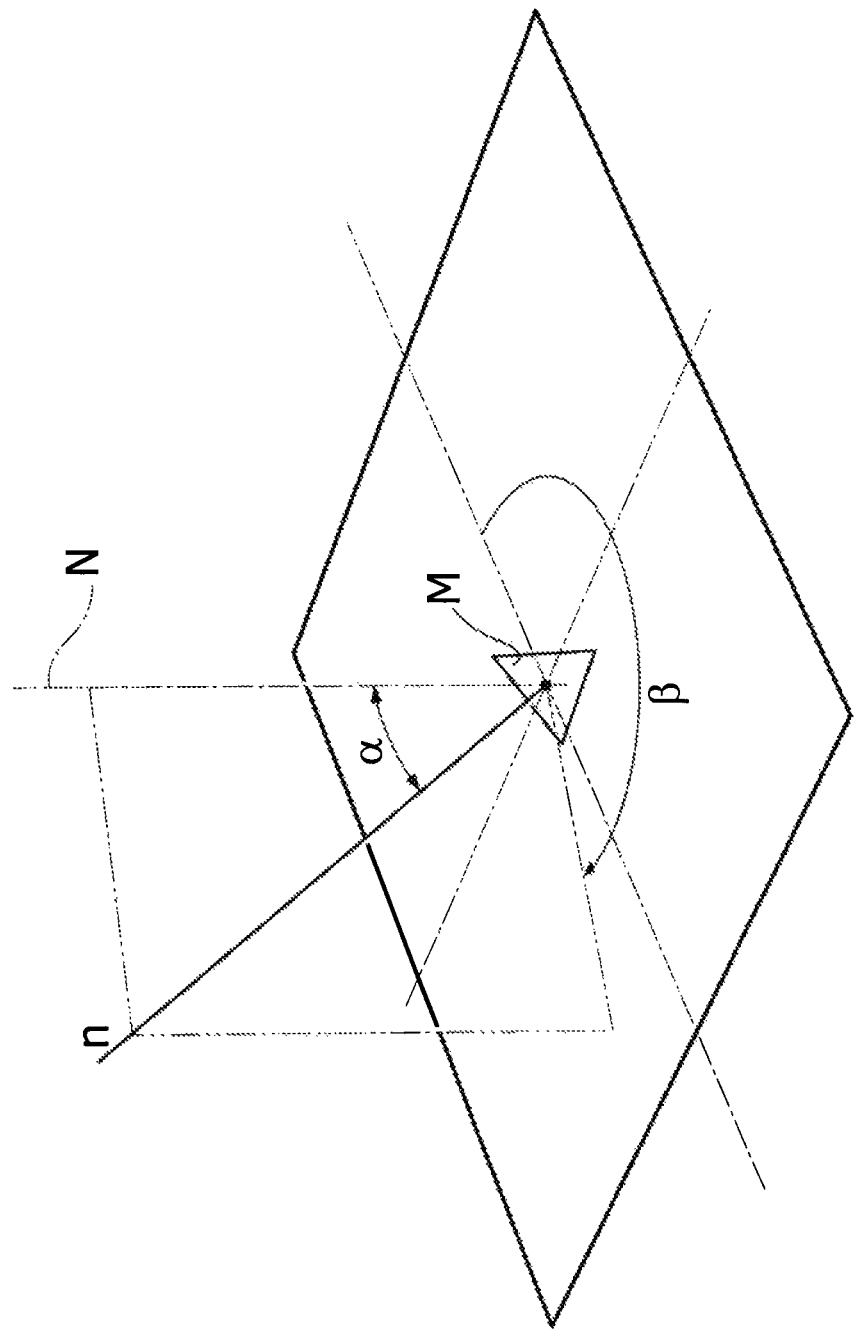
FIG. 4 is a schematic representation of the angles that identify the direction of the local straight line normal to a single microface.

In its most general form, the algorithm is based on two assumptions:

the surface S (FIG. 1) is substantially plane, i.e., it is possible to define a "global" or "supporting" plane, the planarity of which is not altered by the presence of surface roughness; and the surface S can be represented as a series of adjacent microfaces M (FIGS. 3 and 4).

The ultimate purpose of the profilometric analysis is the determination of the probability distribution of the angular orientations of the normals n (FIG. 4) to the aforesaid microfaces M.

The surface analysis with the profilometer is based upon the determination of the height with respect to a reference plane (the general plane of the surface S, see FIG. 3) of a plurality of points of the surface arranged with constant pitch in each of a series of mutually parallel sectional planes orthogonal to the reference plane. The surface of the specimen is approximated as a distribution of plane triangular microfaces M, each having two vertices (for example $p_1$, $p_2$ in FIG. 3) that are constituted by two of the aforesaid points that are adjacent to one another and arranged on the same sectional plane, and the third vertex ($p_0$) is constituted by a point in a parallel and adjacent sectional plane.

On a simplifying hypothesis, there may be considered even just a single series of points arranged at equal distances apart on a single segment (degenerate case). In this simplified case, the profilometric analysis returns as profile a two-dimensional broken line, i.e., a succession of segments having as ends the points measured by the profilometer. This approach is useful in the case where the surface roughness is random so that the information contained in the profile does not vary in a substantial way as the direction of measurement changes (isotropic profile). Given the difference of height $\Delta h$ between the starting point and ending point of each segment and the pitch p of the profilometer, it is straightforward to calculate the angle $\alpha$ comprised between the local normal n (i.e., the normal to the segment considered) and the global normal N, i.e., the normal to the mean plane of the specimen:

$$tg\alpha = \frac{\Delta h}{p}$$

The distribution $D'(\alpha)$ of the angles $\alpha$ thus calculated for the succession of the segments of the profile must be normalized in such a way as to obtain a distribution $D(\alpha)$ that verifies the following condition:

$$\int D(\alpha)\cos\alpha\, d\alpha = 1$$

To obtain this distribution $D(\alpha)$, the distribution $D'(\alpha)$ is divided by a normalization factor $$\text{norm} = 2\pi \int D'(\alpha)\cos\alpha\sin\alpha\, d\alpha$$

so that $$D(\alpha) = \frac{D'(\alpha)}{\text{norm}} = \frac{D'(\alpha)}{2\pi \int D'(\alpha)\cos\alpha\sin\alpha\, d\alpha}$$

In the second case, not simplified, there may, for example, be considered two consecutive points $p_1$ and $p_2$ on the same segment and a point $p_0$ adjacent to one of the previous ones and set on one of the segments adjacent to the first: since only one plane passes through three non-aligned points, the normal vector n of said plane (FIG. 4) can be given by $$\vec{n} = (\vec{p}_2 - \vec{p}_0) \times (\vec{p}_1 - \vec{p}_0)$$

This approach is useful when the surface roughness is anisotropic, i.e., when the information contained in profiles measured in different directions can be different (for example, owing to a roughness of lattice or regular-dotted type).

The angular distribution $D(\alpha, \beta)$ of the angular orientations of the vectors n corresponding to the individual microfaces of the triangular surface M (FIG. 4) is normalized in a way similar to the previous case.

Method of Calculation of the BRDF

General Description of the Algorithm

The algorithm considers the generic function BRDF ($\theta_i$, $\phi_i$, $\theta_o$, $\phi_o$, $\lambda$) depending, i.e., upon the direction of incidence of the rays of light (identified, as shown in FIG. 1, by the angles $\theta_i$, $\phi_i$), the direction of observation (identified, as shown in FIG. 1, by the angles $\theta_o$, $\phi_o$), and the wavelength $\lambda$.

Figure 2:
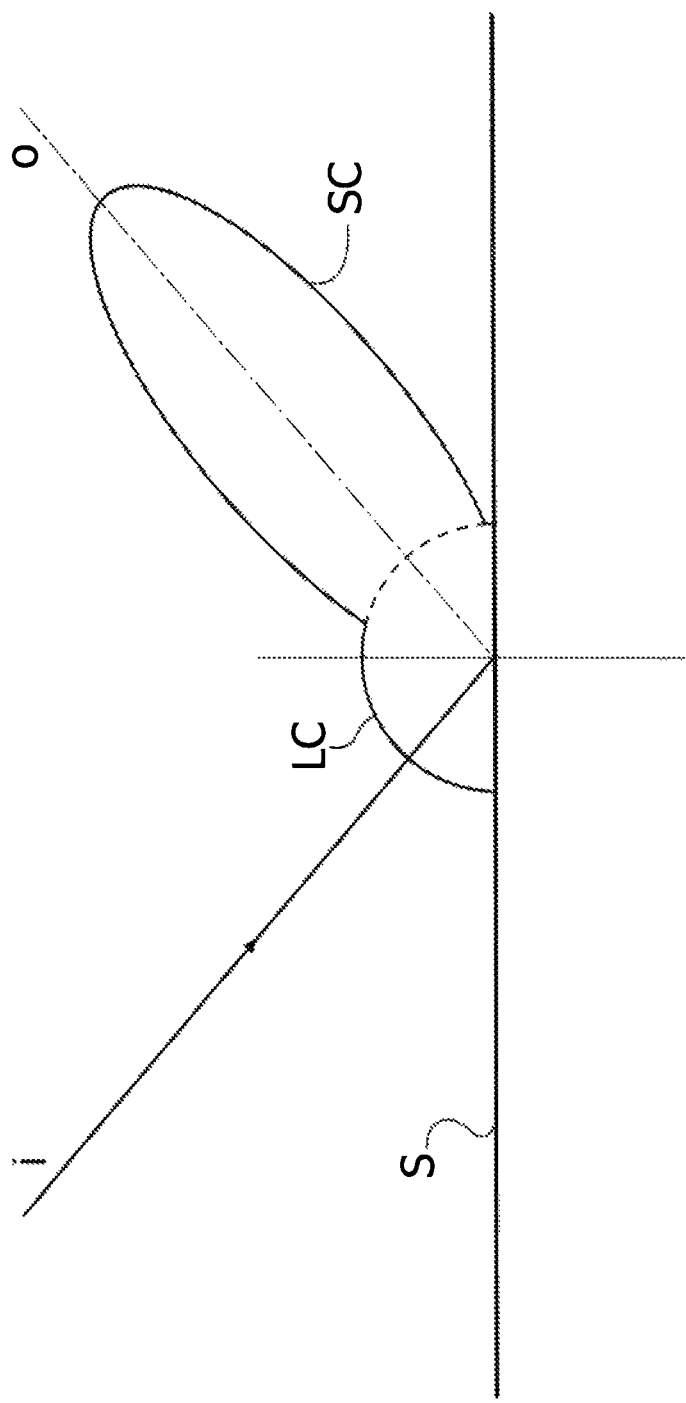
FIG. 2 is a schematic representation of the distribution of light reflected by a point of a rough surface, substantially deriving from the sum of a hemispherical distribution (Lambertian component or component of scattered light) and by an elongated-lobe profile (specular component)

The BRDF is approximated in the form of a sum of a Lambertian component or component of scattered light LC (see the hemispherical portion in FIG. 2) and a specular component SC (see the elongated-lobe portion in FIG. 2). To a first approximation, the component LC may be considered as constant with respect to the directions of incidence and of observation, in so far as it is only a function of the wavelength, whereas the component SC depends upon the directions of incidence and of observation, but is substantially independent of the wavelength (the dependence upon the wavelength of the component SC passes through the dependence upon the wavelength of the value of the refractive index of the material constituting the specimen).

In the method according to the invention, the BRDF is obtained through the following main steps:

for each direction ($\theta_i$, $\phi_i$) of incidence of the light on the surface of the specimen and for each direction of observation ($\theta_o$, $\phi_o$), there is determined the angular orientation ($\alpha$, $\beta$) of the microfaces M that contribute to reflecting in a specular way the light incident in the direction of observation and there is determined, starting from the probability distribution D($\alpha$, $\beta$), the relative numerosity of the microfaces with the orientation ($\alpha$, $\beta$) calculated;

for each direction ($\theta_i$, $\phi_i$) of incidence of the light on the surface of the specimen and for each direction of observation ($\theta_o$, $\phi_o$), there is determined the angle of incidence of the light $\zeta(\theta_i, \phi_i, \theta_o, \phi_o)$ on the aforesaid contributing microfaces M;

on the basis of the angle of incidence of the light $\zeta(\theta_i, \phi_i, \theta_o, \phi_o)$ on the aforesaid contributing microfaces and on the basis of the refractive index n, the Fresnel factor F($\theta_i$, $\phi_i$, $\theta_o$, $\phi_o$) defining the specular reflectance of each microface is determined as the sum of the two Fresnel reflectances $F_s$, $F_p$ for two principal polarization planes $$F = \frac{F_s + F_p}{2}$$

where $$F_s = \left( \frac{n^2 \cdot \cos\zeta - \sqrt{n^2 - \sin^2\zeta}}{n^2 \cdot \cos\zeta - \sqrt{n^2 + \sin^2\zeta}} \right)^2$$

$$F_p = \left( \frac{\cos\zeta - \sqrt{n^2 - \sin^2\zeta}}{\cos\zeta - \sqrt{n^2 + \sin^2\zeta}} \right)^2$$

the specular component SC of the BRDF is calculated as $$SC = \frac{1}{4\cos\vartheta_i \cos\vartheta_o} D(\vartheta_i, \varphi_i, \vartheta_o, \varphi_o) F(\vartheta_i, \varphi_i, \vartheta_o, \varphi_o) G(\vartheta_o)$$

where:

D( ) is the aforesaid probability distribution of the orientation of the microfaces, F( ) is the aforesaid Fresnel factor, and G( ) is a corrective factor of the probability D, which takes into account the effect of masking of the light, reflected from a microface, by the adjacent microfaces, the primary Lambertian component, or primary scattered component, $$\frac{d(\lambda)}{\pi}$$

of the BRDF, which is a function of the wavelength $\lambda$, is evaluated as difference between the spectrum of total reflectance, previously measured on the specimen, and the integral $\int(SC)\cos\theta_o d\Omega$ of the specular component SC calculated previously;

the primary Lambertian component $$\frac{d(\lambda)}{\pi}$$

is corrected by multiplying it by the following compensation factor:

$$\left( 1 - \frac{G(\vartheta_o) D_{flat}(\alpha, \beta)}{4\cos\vartheta_i \cos\vartheta_o} \right)$$

where:

G( ) is the aforesaid masking factor, and $D_{flat}$( ) is a constant probability distribution $D_{flat}(\alpha)$, for which the following condition always applies:

$\int D_{flat}(\alpha) \cos\alpha\, d\alpha = 1$ so as to obtain the Lambertian component LC of the BRDF;

the total BRDF is calculated as the sum of the Lambertian component and of the specular component $$BRDF(\vartheta_i, \varphi_i, \vartheta_o, \varphi_o, \lambda) = LC + SC = \frac{d(\lambda)}{\pi}\left(1 - \frac{G(\vartheta_o)D_{flat}(\alpha, \beta)}{4\cos\vartheta_i\cos\vartheta_o}\right) + \frac{1}{4\cos\vartheta_i\cos\vartheta_o} D(\vartheta_i, \varphi_i, \vartheta_o, \varphi_o) F(\vartheta_i, \varphi_i, \vartheta_o, \varphi_o) G(\vartheta_o).$$

There may be recognized:

in the first addendum of the formulation of the BRDF the Lambertian component, in which there already appears a corrective factor to highlight the effects of masking at wide angles, which will be better illustrated in what follows;

in the second addendum of the formulation of the BRDF the specular component.

In essence, the algorithm for calculation of the BRDF is based on the following consideration: assuming that the surface of the specimen can be represented as plane reflecting microfaces set up against one another (the reflectance being obtained according to the Fresnel laws, hence as a function of the refractive index of the material making up the specimen and of the angle of incidence of the light), each of said faces being characterized by an angular orientation ($\alpha$, $\beta$) of their own normal with respect to the global normal of the specimen, then, given a direction ($\theta_i$, $\phi_i$) of incidence of the light on the surface of the specimen and a direction of observation ($\theta_o$, $\phi_o$), it is possible to obtain trigonometrically the angular orientation ($\alpha$, $\beta$) of the microfaces that can contribute to reflecting in a specular way (with reflectance determined according to Fresnel laws) the light impinging in the direction of observation. The probability distribution $D(\alpha, \beta)$ linked to the orientation of the microfaces is the main factor that determines the intensity of the light reflected specularly in the direction of observation $(\theta_o, \phi_o)$ and, consequently, the shape of the BRDF.

Probability Distribution $D(\alpha, \beta)$ of the Angular Orientation of the Microfaces In the case of the simplifying hypothesis already presented above, where the profile of the surface S is assumed isotropic, it is assumed that the probability distribution $D(\alpha, \beta)$ linked to the orientation of the microfaces is independent of $\beta$ so that the probability distribution of the angular orientation of the microfaces is simplified in a $D(\alpha)$, where $\alpha$ is the angle comprised between the local normal n and the global normal N.

The probability distribution of the angular orientation of the microfaces $D(\alpha)$ may be obtained as described above.

Given the direction $(\theta_i, \phi_i)$ of incidence of the rays that illuminate the surface of the specimen and the direction of observation $(\theta_o, \phi_o)$, it is possible to calculate trigonometrically the angular orientation $(\alpha, \beta)$ of the microfaces, which, behaving in a purely specular way, reflect the light from the direction of incidence of the rays to the direction of observation.

Using a general approach, there may be defined the following directions:

direction of incidence of the rays on the surface $\vec{l}$, characterized by the angles $(\theta_i, \phi_i)$;

direction of observation $\vec{r}$, characterized by the angles $(\theta_o, \phi_o)$;

orientation of the useful microfaces $\vec{n}$, characterized by the angles $(\alpha, \beta)$.

The Snell law for reflection can be written in vector form as $$\vec{r} = -\vec{l} + 2(\vec{n} \cdot \vec{l})\vec{n}$$

whence, known the directions of incidence $\vec{l}$ and of observation $\vec{r}$, it is possible to derive the orientation of the vector $\vec{n}$.

By way of example, there is presented the simplest case where, given that it is possible to invoke the isotropy of the profile, it is assumed that the probability distribution of the angular orientation of the microfaces making up the surface of the specimen depends only upon the angle $\alpha$ comprised between the normal to the microface and the global normal of the surface of the specimen. There is hence obtained only the angle $\alpha$ of the microfaces that contribute to the reflection in the direction of observation $$tg\alpha = \frac{\sqrt{(sen\theta_o \cos\varphi_o - sen\vartheta_i)^2 + sen^2\vartheta_o sen^2\varphi_o}}{\cos\vartheta_o + \cos\vartheta_i}$$

In this way, the dependence of $\alpha$ upon the set of four $(\theta_i, \phi_i, \theta_o, \phi_o)$, and hence the uniqueness in the determination of a given the directions of incidence $(\theta_i, \phi_i)$ and of observation $(\theta_o, \phi_o)$, is rendered explicit. There consequently follows the possibility of expressing $\alpha(\theta_i, \phi_i, \theta_o, \phi_o)$.

In addition to the $D(\alpha)$ described so far, also constant a probability distribution $D_{flat}(\alpha)$ is considered, for which the following condition always applies:

$$\int D_{flat}(\alpha) \cos\alpha\, d\alpha = 1$$

which is useful for determining a corrective factor of the Lambertian component already described above.

In the most complete case, instead, the isotropy of the profile is not invoked, and from the vector formulation it is possible to set alongside the evaluation of $\alpha$ also the evaluation of $\beta$. In this way, the dependence of $\alpha$ and of $\beta$ upon the set of four $(\theta_i, \phi_i, \theta_o, \phi_o)$, and hence the uniqueness in the determination of $\alpha$ and $\beta$ given the directions of incidence $(\theta_i, \phi_i)$ and of observation $(\theta_o, \phi_o)$, is rendered explicit. There consequently follows the possibility of expressing $\alpha(\theta_i, \phi_i, \theta_o, \phi_o)$ and $\beta(\theta_i, \phi_i, \theta_o, \phi_o)$.

Determination of the Fresnel Factor

Given the direction of incidence of the rays $(\theta_i, \phi_i)$ and a direction of observation $(\theta_o, \phi_o)$, and if $\zeta(\theta_i, \phi_i, \theta_o, \phi_o)$ is the angle of incidence of the light on the microfaces that reflect specularly in the direction of observation, i.e., the angle comprised between the local normal and the direction of arrival of the rays, trigonometrically it is possible to obtain $$\sin 2\zeta = \cos\theta_i \cos\theta_o - \sin\theta_i \sin\theta_o \cos\phi_o$$

Given the angle of incidence $\zeta$ and the refractive index n of the material, it is possible to calculate the two Fresnel reflectances for the two principal planes of polarization (i.e., the reflectances due to the discontinuity of the refractive index):

$$F_s = \left(\frac{n^2 \cdot \cos\zeta - \sqrt{n^2 - \sin^2\zeta}}{n^2 \cdot \cos\zeta - \sqrt{n^2 + \sin^2\zeta}}\right)^2$$

$$F_p = \left(\frac{\cos\zeta - \sqrt{n^2 - \sin^2\zeta}}{\cos\zeta - \sqrt{n^2 + \sin^2\zeta}}\right)^2$$

Considering the incident light as not polarized, we can write $$F = \frac{F_s + F_p}{2}$$

The Fresnel factor $F(\zeta)$, which can also be expressed indirectly as $F(\theta_i, \phi_i, \theta_o, \phi_o)$, hence describes the specular reflectance of each microface in the geometrical conditions of observability and constitutes the main corrective factor for the intensity distribution given by the probability distribution $D(\alpha, \beta)$ of the angular orientation of the microfaces.

Masking Factor

The algorithm considers a so-called masking function $G(\theta_o)$ thus described:

$$G(\vartheta_o) = \frac{1}{1 + I(\vartheta_o)}$$

$$I(\vartheta_o) = \begin{cases} \int_{\pi/2-\vartheta_o}^{\pi/2} tg\vartheta_o\left(\alpha - \frac{1}{tg\vartheta_o}\right)D(\alpha)\cos^2\alpha\, d\alpha & \text{if } \frac{tg\alpha}{tg(\pi/2 - \vartheta_o)} > 1 \\ 0 & \text{if } \frac{tg\alpha}{tg(\pi/2 - \vartheta_o)} \le 1 \end{cases}$$

The masking function $G(\theta_o)$, which describes masking of the light, reflected from a microface, by the adjacent microfaces, constitutes a further corrective factor of the intensity distribution determined by the probability distribution $D(\alpha)$ of the angular orientation of the microfaces, already corrected with the Fresnel factor.

Lambertian Component

By definition, the following relation applies:

$$R_{tot}(\theta_i,\phi_i,\lambda)=\int BRDF(\theta_i,\phi_i,\theta_o,\phi_o,\lambda)\cos\theta_o d\Omega$$

i.e., given a direction of incidence of the light ($\theta_i$, $\phi_i$) and a wavelength $\lambda$, the total reflectance (specularity included) is calculated as the integral, extended to the entire solid angle, of the BRDF corrected by the cosine of the angle of observation $\theta_o$.

Having available the following data at input:
refractive index n of the material making up the specimen,
profilometric determination of the surface of the specimen, and
spectrum of total reflectance, specularity included
and considering that:
the function BRDF has been expressed as the sum of a Lambertian component dependent upon the wavelength and of a specular component not dependent upon the wavelength, and
the corrective factor of the Lambertian component can be considered negligible for the purposes of calculation of the reflectance that can be put down just to the Lambertian component we can calculate the integral of the function BRDF:

$$\begin{aligned}R_{tot}(\lambda) &= \int BRDF(\vartheta_i, \varphi_i, \vartheta_o, \varphi_o, \lambda)\cos\vartheta_o d\Omega = \\ &= \int (\text{Lambertian component})\cos\vartheta_o d\Omega + \\ &\quad \int (\text{specular component})\cos\vartheta_o d\Omega = \\ &\cong \frac{d(\lambda)}{\pi} + \int (\text{specular component})\cos\vartheta_o d\Omega\end{aligned}$$

It follows that, if the reflectance spectrum with specularity included and the data necessary for determination of the specular component of the BRDF (refractive index of the material, profilometric determination, and direction of incidence of the rays) are known, it is possible to estimate the Lambertian component in its simplified form $d(a)/n$, alongside which there will be set the corrective factor present in the complete formulation already seen above.

Operating Procedure

Limiting the treatment for simplicity to the isotropic case, once the direction ($\theta_i$, $\phi_i$) of incidence of the rays of light has been defined, for each direction of observation ($\theta_o$, $\phi_o$) there is determined the angular orientation of the contributing microfaces $\alpha(\theta_i, \phi_i, \theta_o, \phi_o)$ and the angle of incidence of the light $\zeta(\theta_i, \phi_i, \theta_o, \phi_o)$ on the contributing microfaces themselves, and hence the Fresnel factor $F(\theta_i, \phi_i, \theta_o, \phi_o)$ is obtained.

Given that the distribution $D[\alpha(\theta_i, \phi_i, \theta_o, \phi_o)]$, the masking factor $G(\theta_o)$, and the component $d(\lambda)$ can be derived from the input data, for each direction of observation it is possible to derive $$BRDF(\vartheta_i, \varphi_i, \vartheta_o, \varphi_o, \lambda) = \\ \frac{d(\lambda)}{\pi}\left(1 - \frac{G(\vartheta_o)D_{flat}(\alpha)}{4\cos\vartheta_i\cos\vartheta_o}\right) + \frac{1}{4\cos\vartheta_i\cos\vartheta_o}D(\alpha)F(\alpha)G(\vartheta_o)$$

Output Data

When the function $BRDF(\theta_i, \phi_i, \theta_o, \phi_o, \lambda)$ has been defined for each angle of incidence of the light ($\theta_i$, $\phi_i$) and for each wavelength $\lambda$, the algorithm can determine the output in different formats. Indicated hereinafter are some formats, by way of non-exhaustive example of the potentialities of the approach:
ASTM format (spectrum of total reflectance with specularity included+non-spectral BRDF);
approximated format (Lambertian component+Gaussian component).

BRDF in ASTM Format

In the first case the ASTM format envisages that the BRDF is declared as the combination of:
spectrum of total reflectance, specularity included, of the surface; and
BRDF in the form $BRDF(\theta_i, \phi_i, \theta_o, \phi_o)$, i.e., not dependent upon the wavelength.

The algorithm reduces the individual functions $BRDF(\theta_i, \phi_i, \theta_o, \phi_o, \lambda)$ dependent upon the wavelength $\lambda$ to a single function $BRDF(\theta_i, \phi_i, \theta_o, \phi_o)$ not dependent upon the wavelength, by applying the following relation:

$$BRDF(\theta_i,\phi_i,\theta_o,\phi_o)=\int BRDF(\theta_i,\phi_i,\theta_o,\phi_o,\lambda)\cdot S(\lambda)d\lambda$$

where $S(\lambda)$ is a weight function dependent upon the wavelength. The $BRDF(\theta_i, \phi_i, \theta_o, \phi_o)$ thus obtained hence represents an average evolution the BRDF in the spectral interval considered, weighted with a weight function. In this way, the set of the functions $BRDF(\theta_i, \phi_i, \theta_o, \phi_o, \lambda)$ representing the evolution of the BRDF for each wavelength are reduced to a single non-spectral $BRDF(\theta_i, \phi_i, \theta_o, \phi_o)$: the relationship existing between the functions $BRDF(\theta_i, \phi_i, \theta_o, \phi_o, \lambda)$ and the functions $BRDF(\theta_i, \phi_i, \theta_o, \phi_o)$ is the same that exists between the functions $BRDF(\theta_i, \phi_i, \theta_0, \phi_o, \lambda)$ measured for each wavelength by the instrument REFLET and the functions BRDF $(\theta_i, \phi_i, \theta_o, \phi_o)$ measured by the instrument in white light, i.e., without interposition of a monochromator along the optical path of the detector.

The algorithm is hence able to reproduce the content of a file in ASTM format, having available the total reflectance, specularity included (input datum of the algorithm), and the $BRDF(\theta_i, \phi_i, \theta_o, \phi_o)$ generated by the algorithm.

BRDF in Lambertian+Gaussian Approximated Format

The function $BRDF(\theta_i, \phi_i, \theta_o, \phi_o, \lambda)$ can be reduced to a simplified format that considers the profile as the sum of:
a Lambertian component with constant evolution with respect to ($\theta_i, \phi_i, \theta_o, \phi_o$) and dependent only upon $\lambda$;
a Gaussian component that approximates the specular component of the
BRDF to a Gaussian function, the evolution of which in the plane of incidence of the light on the specimen is of the type:

$$G(\vartheta) = G_0 e^{-\frac{(\vartheta-\vartheta_i)^2}{2\sigma^2}}$$

i.e., it can be represented as a Gaussian curve centred in the specular direction $\theta_0=\theta_i$ and with amplitude given by the parameter $\sigma$. A more refined version can consider not a single parameter of amplitude $\sigma$, but rather two parameters of amplitude $\sigma_\perp$, $\sigma_=$, which characterize, respectively, the transverse and parallel amplitude of the Gaussian with respect to the plane of incidence of the light on the surface.

In the same way as the integral $$\int BRDF(\theta_i,\phi_i,\theta_o,\phi_o,\lambda)\cdot\cos\theta_o d\Omega = R_{tot}$$

we have $$\int gauss(\theta_o,\phi_o,\sigma_-,\sigma_=)\cdot\cos\theta_o d\Omega = R_{gauss}$$

so that it is possible to describe in a complete way the Gaussian curve representing the specular component not through the definition of the parameter $G_0$, but rather through the declaration of the reflectance that can attributed to the Gaussian component.

In order to describe the BRDF in the approximated format, the algorithm uses a simplified method based upon the mere best fit of each individual function $BRDF(\theta_i, \phi_i, \theta_o, \phi_o, \lambda)$ with respect to the sums of:

- a constant component with respect to the direction of observation $(\theta_o, \phi_o)$
- a Gaussian component centred in $\theta_o = \theta_i$ and characterized by the parameters:
  $FWHM_\perp$
  $FWHM_=$
  $G_0$ The Gaussian component can thus be completely described using the parameters referred to above. Alternatively, it is possible, in an approximated way, to consider the parameters:
$FWHM_\perp$
$FWHM_=$
$R_{gauss}$ where $R_{gauss}$ is the part of the overall reflectance that can be attributed to the Gaussian specular component: to a first approximation said reflectance can be estimated using the Fresnel laws.

Calculation of the Gloss

As further output datum it is possible, starting from the non-spectral function $BRDF(\theta_i, \phi_i, \theta_o, \phi_o)$, to estimate the value of the gloss, evaluated according to the ASTM D523-08 standard.

For said purpose, the algorithm evaluates the integral of the non-spectral function $BRDF(\theta_i, \phi_i, \theta_o, \phi_o)$ in the neighbourhood of the direction of examination, setting as angular extremes of integration those indicated by the aforesaid ASTM standard, and calculating the ratio between said integral and the reflectance (evaluated using the Fresnel laws) of a reference plastic specimen with refractive index 1.567.

$$gloss = \frac{\int_{\Omega_{norma}} BRDF(\vartheta_i, \varphi_i, \vartheta_o, \varphi_o, \lambda) \cos\vartheta_o \, d\Omega}{R_{Fresnel}(\vartheta_{gloss})}$$

Of course, without prejudice to the principle of the invention, the details of construction and the embodiments may vary widely with respect to what is described and illustrated herein purely by way of example, without thereby departing from the scope of the present invention.

Determination of the bidirectional transmittance distribution function (BTDF) of a surface.

In the case where the material is transparent, it is possible to characterize with the "bidirectional transmittance function" the scattering properties of each single surface of the specimen (in the classic case of a transparent specimen, the overall scattering lobe is given by the combination of the BTDF of each of the two surfaces).

The determination of the BTDF of each single surface can be carried out in a way altogether similar to the method previously described: limiting for simplicity the analysis to the isotropic case, once the direction $(\theta_i, \phi_o)$ of incidence of the rays of light has been defined, for each direction of observation $(\theta_o, \phi_o)$ the angular orientation of the contributing microfaces $\alpha(\theta_i, \phi_i, \theta_o, \phi_o)$ is determined (taking into account not the laws of the reflection, but Snell laws for refraction and the angle of incidence of the light $\zeta(\theta_i, \phi_i, \theta_o, \phi_o)$ on the same contributing microfaces, whence the Fresnel factor $F(\theta_i, \phi_i, \theta_o, \phi_o)$ is obtained for evaluation of the local transmittance).

Given that the distribution $D[\alpha(\theta_i, \phi_i, \theta_o, \phi_o)]$, the masking factor $G(\theta_o)$, and the component $d(\lambda)$ can be derived from the input data, it is possible to derive for each direction of observation $$BTDF(\vartheta_i, \varphi_i, \vartheta_o, \varphi_o, \lambda) = \frac{d(\lambda)}{\pi}\left(1 - \frac{G(\vartheta_o)D_{flat}(\alpha)}{4\cos\vartheta_i\cos\vartheta_o}\right) + \frac{1}{4\cos\vartheta_i\cos\vartheta_o}D(\alpha)F(\alpha)G(\vartheta_o)$$

What is claimed is:

1. A method for use in designing an automobile dashboard, wherein the method comprises the following steps:
   a1) determining a refractive index of an opaque plastic material forming a portion of a dashboard of a vehicle using an ellipsometer;
   a2) measuring a spectrum of total reflectance on the material using a spectrophotometer; and
   a3) determining a geometry of the profile of said material by:
      a3.1) detecting a height with respect to a reference plane of a plurality of points of the material arranged with constant pitch in each of a series of mutually parallel sectional planes orthogonal to the reference plane using a profilometer; and
      a3.2) approximating the surface of the material as a distribution of plane triangular microfaces, each having two vertices that are constituted by two of the aforesaid points that are adjacent to one another and arranged on the same sectional plane, and the third vertex is constituted by a point in a parallel and adjacent sectional plane;
   b) determining, for each direction $(\theta_i, \phi_i)$ of incidence of the light on the surface of the specimen and for each direction of observation $(\theta_o, \phi_o)$, the angular orientation $(\alpha, \beta)$ of the microfaces contributing to reflecting in a specular way the light incident in the direction of observation and determining the probability distribution $D(\alpha, \beta)$ of the angular orientation of the aforesaid microfaces;
   c) determining, for each direction $(\theta_i, \phi_i)$ of incidence of the light on the surface of the specimen and for each direction of observation $(\theta_o, \phi_o)$, the angle of incidence of the light $\zeta(\theta_i, \phi_i, \theta_o, \phi_o)$ on the aforesaid contributing microfaces;
   d) on the basis of the angle of incidence of the light $\zeta(\theta_i, \phi_i, \theta_o, \phi_o)$ on the aforesaid contributing microfaces, and on the basis of the refractive index n, determining the Fresnel factor $F(\theta_i, \phi_i, \theta_o, \phi_o)$ defining the specular reflectance of each microface, as the sum of the two Fresnel reflectances $F_s$, $F_p$ for two principal planes of polarization:

$$F = \frac{F_s + F_p}{2}$$

where $$F_s = \left(\frac{n^2 \cdot \cos\zeta - \sqrt{n^2 - \sin^2\zeta}}{n^2 \cdot \cos\zeta - \sqrt{n^2 + \sin^2\zeta}}\right)^2$$

-continued $$F_p = \left(\frac{\cos\zeta - \sqrt{n^2 - \sin^2\zeta}}{\cos\zeta - \sqrt{n^2 + \sin^2\zeta}}\right)^2$$

e) circulating the specular component SC of the BRDF as:

$$SC = \frac{1}{4\cos\vartheta_i\cos\vartheta_o}D(\vartheta_i, \varphi_i, \vartheta_o, \varphi_o)F(\vartheta_i, \varphi_i, \vartheta_o, \varphi_o)G(\vartheta_o)$$

where:
D is the aforesaid probability distribution of the orientation of the microfaces;
F is the aforesaid Fresnel factor; and
G is a corrective factor of the probability D, which takes into account the effect of masking of the light, reflected from a microface, by the adjacent microfaces;
f) evaluating the primary Lambertian component, or primary scattered component, $$\frac{d(\lambda)}{\pi}$$

of the bidirectional reflectance distribution function (BRDF), which is a function of the wavelength $\lambda$, as difference between the spectrum of the total reflectance, previously measured on the specimen, and the integral $\int(SC)\cos\theta_o d\Omega$ of the specular component SC calculated previously;
g) correcting the primary Lambertian component $$\frac{d(\lambda)}{\pi},$$

multiplying it by the following compensation factor:

$$\left(1 - \frac{G(\vartheta_o)D_{flat}(\alpha, \beta)}{4\cos\vartheta_i\cos\vartheta_o}\right)$$

where:
G is the aforesaid masking factor; and
$D_{flat}$ is a constant probability distribution $D_{flat}(\alpha)$, for which the following condition always applies:

$$\int D_{flat}(\alpha)\cos\alpha d\alpha = 1$$

so as to obtain the Lambertian component LC of the BRDF;
h) calculating the total BRDF as the sum of the Lambertian component and of the specular component:

$$BRDF(\vartheta_i, \varphi_i, \vartheta_o, \varphi_o, \lambda) = LC + SC = \frac{d(\lambda)}{\pi}\left(1 - \frac{G(\vartheta_o)D_{flat}(\alpha, \beta)}{4\cos\vartheta_i\cos\vartheta_o}\right) +$$

$$\frac{1}{4\cos\vartheta_i\cos\vartheta_o}D(\vartheta_i, \varphi_i, \vartheta_o, \varphi_o)F(\vartheta_i, \varphi_i, \vartheta_o, \varphi_o)G(\vartheta_o)$$

determining if the total BRDF is compatible with requirements of good visibility for a driver of the vehicle to aid in designing the dashboard of the vehicle.

2. The method according to claim 1, wherein the aforesaid masking factor G is given as $$G(\vartheta_o) = \frac{1}{1 + I(\vartheta_o)}$$

where $$I(\vartheta_o) = \begin{cases} \int_{\pi/2-\vartheta_o}^{\pi/2} tg\vartheta_o\left(\alpha - \frac{1}{tg\vartheta_o}\right)D(\alpha)\cos^2\alpha d\alpha & se\, \frac{tg\alpha}{tg(\pi/2-\vartheta_o)} > 1 \\ 0 & se\, \frac{tg\alpha}{tg(\pi/2-\vartheta_o)} \le 1 \end{cases}.$$

3. The method according to claim 1, wherein determining the probability distribution D of the orientation of the microfaces, it is assumed that it is independent of $\beta$ so that said distribution is considered a function only of the angle comprised between the local normal to the individual microface and the normal to the general plane of the surface.

* * * * *